(12) United States Patent
Robichaud et al.

(10) Patent No.: US 11,517,333 B2
(45) Date of Patent: Dec. 6, 2022

(54) PREDRILLING GUIDE FOR KNEE OSTEOTOMY FIXATION PLATE

(71) Applicant: LABORATOIRES BODYCAD INC., Québec (CA)

(72) Inventors: Jean Robichaud, St Aubert (CA); Hugo Robichaud, Quebec (CA)

(73) Assignee: LABORATOIRES BODYCAD INC., Québec (CA)

( * ) Notice: Subject to any disclaimer, the term of this patent is extended or adjusted under 35 U.S.C. 154(b) by 330 days.

(21) Appl. No.: 16/609,964

(22) PCT Filed: Aug. 22, 2019

(86) PCT No.: PCT/CA2019/051157
§ 371 (c)(1),
(2) Date: Oct. 31, 2019

(87) PCT Pub. No.: WO2020/037425
PCT Pub. Date: Feb. 27, 2020

(65) Prior Publication Data
US 2021/0353312 A1    Nov. 18, 2021

Related U.S. Application Data

(60) Provisional application No. 62/722,403, filed on Aug. 24, 2018, provisional application No. 62/722,470, filed on Aug. 24, 2018.

(51) Int. Cl.
  *A61B 17/17*  (2006.01)
  *A61B 34/10*  (2016.01)
  *A61B 17/56*  (2006.01)

(52) U.S. Cl.
  CPC ...... *A61B 17/1764* (2013.01); *A61B 17/1728* (2013.01); *A61B 34/10* (2016.02);
  (Continued)

(58) Field of Classification Search
  CPC ... A61B 17/17; A61B 17/1764; A61B 17/171; A61B 17/1728; A61B 2034/104;
  (Continued)

(56) References Cited

U.S. PATENT DOCUMENTS 2,002,021 A    5/1935  Rouse
5,620,448 A    4/1997  Puddu
(Continued)

FOREIGN PATENT DOCUMENTS

| CN | 103393459 A | 11/2013 |
| CN | 207721848 U | 8/2018 |
| WO | 2015003284 A2 | 1/2015 |

OTHER PUBLICATIONS

Azernikov S. (2013) Inhomogeneous Axial Deformation for Orthopedic Surgery Planning. In: Csurka G., Kraus M., Mestetskiy L., Richard P., Braz J. (eds) Computer Vision, Imaging and Computer Graphics. Theory and Applications. VISIGRAPP 2011. Communications in Computer and Information Science, vol. 274, p. 69-85. Springer, Berlin, Heidelberg.

(Continued)

*Primary Examiner* — Kevin T Truong
*Assistant Examiner* — Diana Jones
(74) *Attorney, Agent, or Firm* — Marshall, Gerstein & Borun LLP

(57) ABSTRACT

A guide for guiding drill bits to form holes in a bone in a predetermined pattern for receiving fasteners to secure an implant to the bone is provided. The guide includes a guide body having a bone interface side opposite an operative side, the bone interface side having a bone contacting surface engageable with a surface of the bone. The guide also includes a plurality of drill guides extending from the operative side of the guide body for guiding corresponding drill bits, wherein the bone contacting surface of the guide
(Continued)

body is configured to substantially conform to surface contours of the bone at a predetermined position on the bone. A method of designing the guide is also provided.

18 Claims, 4 Drawing Sheets

(52) U.S. Cl.
CPC ... *A61B 2017/568* (2013.01); *A61B 2034/104* (2016.02); *A61B 2034/105* (2016.02); *A61B 2034/108* (2016.02)

(58) Field of Classification Search
CPC ........ A61B 2034/105; A61B 2034/108; A61B 2017/568
See application file for complete search history.

(56) References Cited

U.S. PATENT DOCUMENTS

| | | |
|---|---|---|
| 5,749,875 A | 5/1998 | Puddu |
| 6,017,342 A | 1/2000 | Rinner |
| 6,066,142 A | 5/2000 | Serbousek et al. |
| 6,461,359 B1 | 10/2002 | Tribus et al. |
| 7,794,467 B2 | 9/2010 | McGinley et al. |
| 7,935,119 B2 | 5/2011 | Ammann et al. |
| 8,083,746 B2 | 12/2011 | Novak |
| 8,092,465 B2 | 1/2012 | Meizger et al. |
| 8,137,406 B2 | 3/2012 | Novak et al. |
| 8,211,112 B2 | 7/2012 | Novak et al. |
| 8,241,292 B2 | 8/2012 | Collazo |
| 8,241,293 B2 | 8/2012 | Stone et al. |
| 8,337,507 B2 | 12/2012 | Lang et al. |
| 8,388,690 B2 | 3/2013 | Singhatat et al. |
| 8,409,209 B2 | 4/2013 | Ammann et al. |
| 8,484,001 B2 | 7/2013 | Glozman et al. |
| 8,594,395 B2 | 11/2013 | Roose et al. |
| 8,632,547 B2 | 1/2014 | Maxson et al. |
| 8,709,052 B2 | 4/2014 | Ammann et al. |
| 8,753,348 B2 | 6/2014 | DiDomenico et al. |
| 8,828,087 B2 | 9/2014 | Stone et al. |
| 8,979,866 B2 | 3/2015 | Patel et al. |
| 8,998,903 B2 | 4/2015 | Price et al. |
| 9,014,835 B2 | 4/2015 | Azernikov et al. |
| 9,072,555 B2 | 7/2015 | Michel |
| 9,456,833 B2 | 10/2016 | Maxson et al. |
| 9,480,490 B2 | 11/2016 | Meizger et al. |
| 9,486,228 B2 | 11/2016 | Saw et al. |
| 9,603,605 B2 | 3/2017 | Collazo |
| 9,687,261 B2 | 6/2017 | Serbousek et al. |
| 9,707,023 B2 | 7/2017 | Ammann et al. |
| 9,770,302 B2 | 9/2017 | Kang et al. |
| 9,814,533 B2 | 11/2017 | Park et al. |
| 9,833,245 B2 | 12/2017 | Maxson |
| 9,877,758 B2 | 1/2018 | Michel |
| 9,877,790 B2 | 1/2018 | Bojarski et al. |
| 9,943,348 B2 | 4/2018 | Schelling |
| 10,245,089 B2 | 4/2019 | Paik |
| 2005/0209599 A1 | 9/2005 | Brunsvold |
| 2006/0052795 A1 | 3/2006 | White |
| 2007/0191848 A1 | 8/2007 | Wack et al. |
| 2009/0082816 A1 | 3/2009 | Graham et al. |
| 2011/0213376 A1* | 9/2011 | Maxson ............. A61B 17/8095 606/88 |
| 2013/0338673 A1* | 12/2013 | Keppler ............. A61B 17/1778 606/86 R |
| 2015/0051650 A1 | 2/2015 | Verstreken et al. |
| 2015/0088143 A1* | 3/2015 | Lipman .............. A61B 17/1764 606/88 |
| 2015/0196308 A1* | 7/2015 | Wilkinson ........... A61B 17/157 606/88 |
| 2015/0305752 A1* | 10/2015 | Eash .................. A61B 17/8095 606/88 |
| 2016/0095634 A1 | 4/2016 | Meyer |
| 2016/0113784 A1 | 4/2016 | Robichaud |
| 2016/0174994 A1* | 6/2016 | Hafez ................ A61B 17/1721 606/88 |
| 2016/0192949 A1* | 7/2016 | Robichaud ............ A61F 2/4603 606/87 |
| 2016/0235454 A1 | 8/2016 | Treace et al. |
| 2017/0325823 A1 | 11/2017 | Phillips-Hungerford et al. |
| 2017/0325826 A1 | 11/2017 | Bake et al. |
| 2018/0344326 A1* | 12/2018 | Chan ..................... A61B 34/10 |

OTHER PUBLICATIONS

International Search Report and Written Opinion for Application No. PCT/CA2019/051147, dated Oct. 15, 2019.
International Search Report and Written Opinion for Application No. PCT/CA2019/051148, dated Oct. 24, 2019.
International Search Report and Written Opinion for Application No. PCT/CA2019/051149, dated Oct. 7, 2019.
International Search Report and Written Opinion for Application No. PCT/CA2019/051151, dated Oct. 22, 2019.
International Search Report and Written Opinion for Application No. PCT/CA2019/051153, dated Sep. 25, 2019.
International Search Report and Written Opinion for Application No. PCT/CA2019/051156, dated Sep. 30, 2019.
International Search Report and Written Opinion for Application No. PCT/CA2019/051157, dated Oct. 25, 2019.

* cited by examiner

PREDRILLING GUIDE FOR KNEE OSTEOTOMY FIXATION PLATE

CROSS-REFERENCE TO RELATED APPLICATIONS

This application claims priority under 35USC § 119(e) of U.S. Provisional Application No. 62/722,470, filed Aug. 24, 2018, entitled "PREDRILLING GUIDE FOR KNEE OSTEOTOMY FIXATION PLATE", and of U.S. Provisional Application No. 62/722,403, filed Aug. 24, 2018, entitled "SURGICAL KIT FOR KNEE OSTEOTOMIES AND CORRESPONDING PREOPERATIVE PLANNING METHOD", the entirety of which are hereby incorporated by reference.

TECHNICAL FIELD

The technical field generally relates to tools used in knee osteotomy procedures, and more particularly in high tibial osteotomies.

BACKGROUND

Knee osteotomies are orthopedic procedures which aim to correct the alignment of knee joints to adjust pressure distribution. A high tibial osteotomy is a type of knee osteotomy which involves correcting the alignment of a knee joint by reconfiguring the mechanical axis of the tibia. Depending on the required correction angle, the high tibial osteotomy can be an open wedge osteotomy or a closed wedge osteotomy. In an open wedge osteotomy, a planar cut is made in the tibia below the knee, and the tibia bone is opened along the planar cut to form a wedge-shaped opening with a specified angle. In a closed wedge osteotomy, a wedge of bone having a specified angle is removed from the tibia bone below the knee, and the tibia bone is closed along the wedge. After the bone is opened or closed, it is retained in place by installing a fixation plate. The opening or closing effectively adjusts the angle of the tibia relative to the femur, thereby reconfiguring how pressure between the tibia and the femur is distributed in the knee.

Existing tools and procedures are limited in the accuracy and precision with which the alignment of the knee can be corrected. There is therefore much room for improvement.

SUMMARY

According to an aspect, a guide for guiding drill bits to form holes in a bone in a predetermined pattern for receiving fasteners to secure an implant to the bone, the guide including: a guide body having a bone interface side opposite an operative side, the bone interface side including a bone contacting surface engageable with a surface of the bone; and a plurality of drill guides extending from the operative side of the guide body for guiding corresponding drill bits; wherein the bone contacting surface of the guide body is configured to substantially conform to surface contours of the bone at a predetermined position on the bone.

According to an aspect, a method is provided for designing a guide for guiding drill bits to form holes in a bone in a predetermined pattern for securing a knee osteotomy implant on the bone prior to altering a geometry of the bone. The method includes the steps of: creating a digital 3D model of the bone; virtually cutting the 3D model of the bone to form a planar cut therein; virtually opening the 3D model of the bone along the planar cut to a desired opening angle; virtually positioning an implant and corresponding fasteners on the 3D model of the bone to set final positions of drill holes; virtually closing the 3D model of the bone to determine corresponding initial positions of the drill holes; and designing the guide with drill guides positioned according to the initial positions of the drill holes.

According to an aspect, a guide is provided for assisting in forming holes in a bone according to a predetermined pattern for receiving fasteners to secure an implant on the bone. The guide includes: a guide body having a bone interface side opposite an operative side, the bone interface side comprising a bone contacting surface engageable with a surface of the bone; and a plurality of drill guides connected to the operative side of the guide body for guiding corresponding drill bits adapted to form the holes, wherein the drill guides are positioned to guide drill bits to form holes in the bone in initial positions prior to a planned alteration of a geometry of the bone which will cause the drill holes to move into final positions in alignment with fastener apertures in the implant.

According to a possible embodiment, the guide is custom made according to the anatomy of the bone such that the bone contacting surface substantially conforms to surface contours of the bone at a predetermined position on the bone.

According to a possible embodiment, each drill guide includes a guide barrel extending from the operative side along a lengthwise axis and terminating at a terminal end.

According to a possible embodiment, the guide barrels extend from the operative side at predetermined angles and are positioned on the operative side according to the predetermined pattern.

According to a possible embodiment, the guide barrels are adapted to limit insertion depth of the drill bits for forming holes in the bone having a predetermined depth.

According to a possible embodiment, each guide barrel includes sidewalls defining a guide tunnel extending through the guide barrel along the lengthwise axis, the guide tunnel having openings on the bone interface side and operative side of the guide body configured to receive a corresponding drill bit therethrough.

According to a possible embodiment, the sidewalls are adapted to constrain movement of the drill bit to a predetermined depth, position and/or orientation relative to the bone.

According to a possible embodiment, the guide further includes a handle member connected to the guide body adapted to facilitate manipulation and positioning of the guide body.

According to a possible embodiment, the handle member is a rigid elongated member extending from the operative side of the guide body.

According to a possible embodiment, the guide body further includes fastener apertures for receiving fasteners to secure the guide body to the bone.

According to a possible embodiment, the guide barrels are positioned to assist in forming holes on either side of a planar cut formed in the bone.

According to a possible embodiment, the guide body includes an alignment mechanism configured to engage with an anchor module secured on a surface of the bone and spanning transversely across the planar cut.

According to a possible embodiment, the alignment mechanism includes an attachment interface for respectively interfacing with anchoring points of the anchoring module positioned on either side of the planar cut.

According to a possible embodiment, the attachment interface is configured to interface with the anchoring points in only one orientation.

According to a possible embodiment, the anchoring points include apertures, and wherein the attachment interface comprises protrusions configured to respectively engage in the apertures.

According to a possible embodiment, the guide is made from a rigid material.

According to a possible embodiment, the guide is made from 3D-printable material.

According to an aspect, a guide is provided for guiding drill bits to form holes in a bone in a predetermined pattern for receiving fasteners to secure an implant to the bone. The guide includes: a guide body having a bone interface side opposite an operative side, the bone interface side comprising a bone contacting surface engageable with a surface of the bone; a plurality of drill guides extending from the operative side of the guide body for guiding corresponding drill bits; and an alignment mechanism connected to the guide body for engaging with anchoring points on the bone to secure the guide body in a predetermined position relative to the bone, wherein the bone contacting surface of the guide body is configured to substantially conform to surface contours of the bone at a predetermined position on the bone.

According to a possible embodiment, wherein each drill guide includes a guide barrel extending from the operative side along a lengthwise axis and terminating at a terminal end.

According to a possible embodiment, the guide barrels extend from the operative side at predetermined angles and are positioned on the operative side according to the predetermined pattern.

According to a possible embodiment, the guide barrels are adapted to limit insertion depth of the drill bits for forming holes in the bone having a predetermined depth.

According to a possible embodiment, each guide barrel includes sidewalls defining a guide tunnel extending through the guide barrel along the lengthwise axis, the guide tunnel having openings on the bone interface side and operative side of the guide body configured to receive a corresponding drill bit therethrough.

According to a possible embodiment, the sidewalls are adapted to constrain movement of the drill bit to a predetermined depth, position and/or orientation relative to the bone.

According to a possible embodiment, the guide further includes a handle member connected to the guide body adapted to facilitate manipulation and positioning of the guide body.

According to a possible embodiment, the handle member is a rigid elongated member extending from the operative side of the guide body.

According to a possible embodiment, the guide body further includes fastener apertures for receiving fasteners to secure the guide body to the bone.

According to a possible embodiment, the guide barrels are positioned to assist in forming holes on either side of a planar cut formed in the bone.

According to a possible embodiment, the alignment mechanism is configured to engage with anchoring points on the surface of the bone on either sides of the planar cut.

According to a possible embodiment, the anchoring points include apertures, and wherein the alignment mechanism comprises protrusions configured to respectively engage in the apertures.

According to a possible embodiment, the alignment mechanism is configured to engage the anchoring points in only one orientation.

According to a possible embodiment, the guide is configured to assist in forming holes in the bone prior to a altering a geometry of the bone.

According to a possible embodiment, the guide body is adapted to span across an opening formed along the planar cut, and comprises a proximal section positioned above the opening and a distal section positioned below the opening.

According to a possible embodiment, the guide body further includes an intermediate section spanning the opening between the proximal and distal sections, and an alignment mechanism extending from the intermediate section for engaging the bone to secure the guide body in a predetermined position relative to the bone.

According to a possible embodiment, the alignment mechanism includes a wedge extending from the intermediate section adapted to be inserted within the opening.

According to a possible embodiment, the wedge includes contours configured to match inner surface contours of the opening.

DETAILED DESCRIPTION

Figure 1:
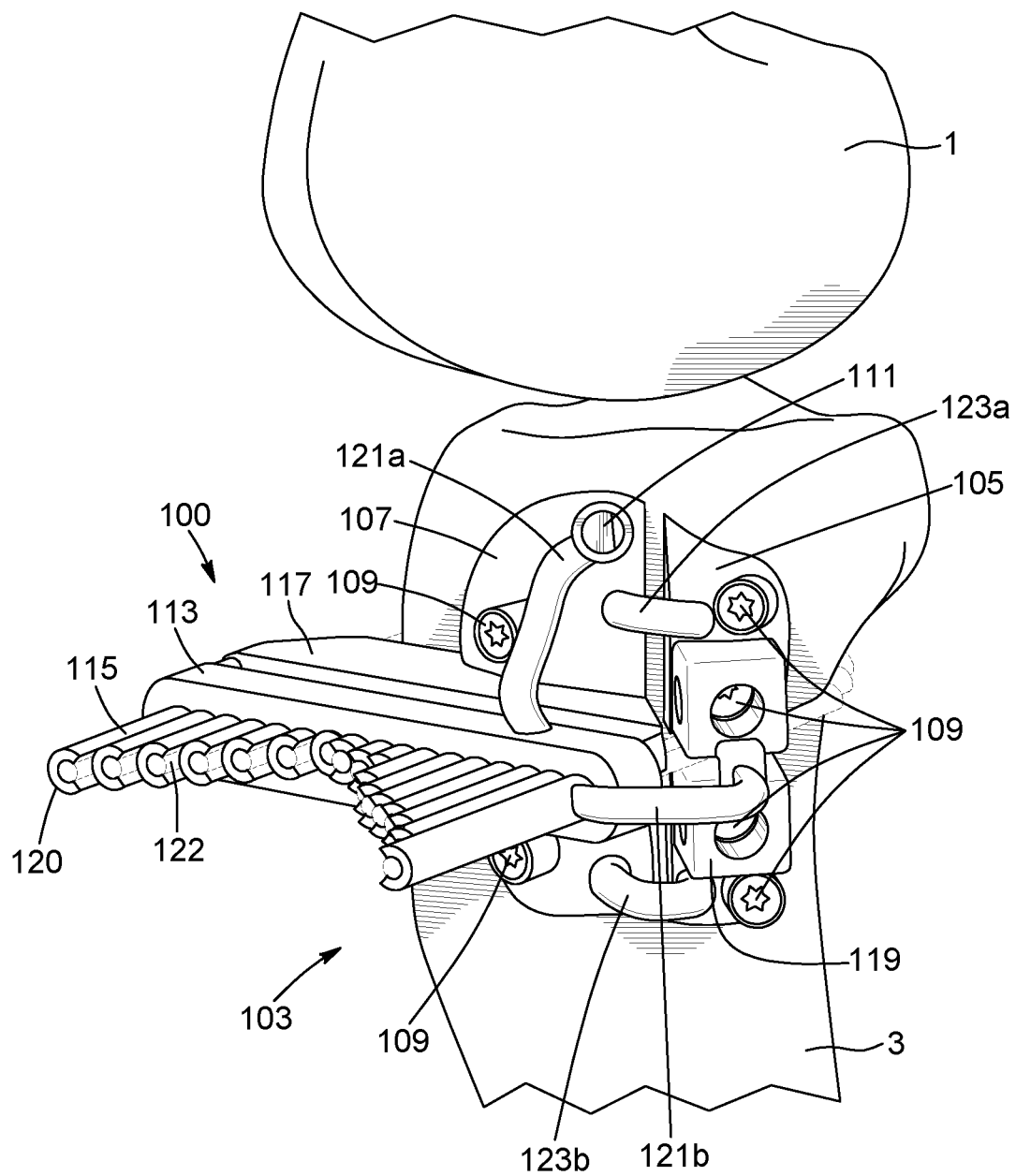
FIG. 1 is a perspective view of a surgical guide secured to a patient's tibia bone, according to an embodiment.

With reference to FIG. 1, a surgical guide 100 is provided. The surgical guide 100 is configured to be mounted to a patient's tibia bone 3 and includes a plurality of modules to guide various surgical tools used throughout the osteotomy procedure. The surgical guide 100 is patient-specific in that it is designed and manufactured according to the specific anatomy of a patient. In this fashion, the surgical guide 100 can be shaped and configured such that it can fit precisely on a predetermined position on the patient's bone 3 and be secured thereto to assure proper alignment of guides for various surgical tools. In the present embodiment, the surgical guide 100 has a body made from 3D printed plastic, although it is appreciated that other biocompatible materials compatible with other custom manufacturing methods are also possible.

The body of surgical guide 100 comprises a bone interface side 101 for facing the patient's bone 3, and an operative side 103 for facing away from the patient's bone 3. In the present embodiment, bone interface side 101 is configured to be positioned directly on the patient's bone, and comprises a surface having contours complementary is shape to the surface contours of a predetermined area of the patient's bone 3. In this configuration, bone interface side 101 can abut against the patient's bone, and key into a specific position thereon. In the present embodiment, bone interface side 101 comprises a solid surface, however it is appreciated that other configurations are possible. For example, the surface can be defined by an open lattice, and can comprise edges conforming to the contours of the patient's bone 3.

Operative side 103 is provided opposite interface side 101 and includes a variety of components for interacting with surgical tools, as will be described in more detail hereinafter.

In the present embodiment, the body of surgical guide 100 is subdivided into two separable sections, including a lateral section 105 for securing relative to a lateral or medial surface of the patient's bone 3 and an anterior section 107 for securing relative to an anterior surface of the patient's bone 3. It is appreciated, however, that in other embodiments, more or fewer sections are possible to secure relative to different surfaces of the patient's bone 3 depending on surgical requirements. In the present embodiment, lateral section 105 and anterior section 107 are independently securable relative to the patient's bone 3. In this fashion, the lateral 105 or anterior 107 section can be removed from the patient's bone 3 when no longer needed, while the other section can remain secured in place. In the present embodiment, lateral 105 and anterior 107 sections are secured directly to the patient's bone, however it is appreciated that in some embodiments, only one of the lateral 105 and anterior 107 need be affixed directly to the bone. For example, lateral section 105 can be affixed directly to the bone 3, whereas anterior section 107 can be removably attached to lateral section 105 such that it is secured relative the patient's bone 3 without being directly affixed thereto.

In the present embodiment, lateral 105 and anterior 107 sections comprise bone-conforming plates secured to the patient's bone 3 via fasteners. The fasteners comprise surgical screws 109 although it is appreciated that other types of fastening mechanisms are also possible. The screws 109 engage in the patient's bone 3 through canals 110 opening on the bone interface 101 and operative 103 sides of the surgical guide 100. The canals 110 comprise sidewalls extending along a length for guiding insertion of screws 109 through canals 110 at a specified angle and depth. In this fashion, screws 109 drilled into the patient's bone 3 through canals 110 can be guided into a predetermined position, orientation and depth such that they can secure patient-specific surgical guide 100 to the patient's bone 3 in an optimal fashion, and such that the screws 109 will not interfere with tools used during subsequent steps during the osteotomy procedure. The sidewalls of canals 110 can further be configured to abut against a head of screw 109 to block the screw 109 from being inserted too deep into the patient's bone 3.

In the present embodiment, a plurality of canals 110 are provided for securing the surgical guide 100 to the patient's bone 3 via a plurality of screws 109 at strategic locations. It is appreciated, however, that in other embodiments, a different number of screws 109 and canals 110 can be provided, and that they can be positioned and oriented differently depending on the patient's specific anatomy and according to the planned procedure. Moreover, in the present embodiment, each of screws 109 is the same size, but it is appreciated that in other embodiments, different sized screws can be used to secure different parts of the surgical guide 100, and that the canals 110 can be sized and shaped accordingly. Finally, although the screws 109 are guided by canals 110 in the present embodiment, it is appreciated that other screw-guiding mechanisms are possible in other embodiments.

As mentioned above, lateral 105 and anterior 107 sections are separable from one another. In the present embodiment, lateral 105 and anterior 107 sections are generally disjointed from one another and are connected via connecting members. In other words, lateral 105 and anterior 107 sections are not directly fused together, and instead comprise separate spaced-apart sections removably secured to one another at a finite number of fixed points. In this configuration, each of lateral 105 and anterior 107 sections define two separate bone-contacting surfaces including two bone-conforming plates on bone interface side 101 of surgical guide 100. It is appreciated, however, that in other embodiments, lateral 105 and anterior 107 sections can together form a single coherent surface or plate for contacting the bone 3.

Connecting members 121, 123, can be provided to removably connect different sections of the surgical guide 100. In the present embodiment, the lateral 105 and anterior 107 sections are connected to one another at three fixed points via connecting members 121b, 123a and 123b. The connecting members 121b, 123a, 123b are stems comprising narrow strands of rigid material connected at a first end to the lateral section 105 and at a second end to the anterior section 107. The connecting members 121b, 123a, 123b are fused to lateral 105 and anterior 107 sections and/or are formed as integral parts thereof. In this fashion, lateral 105 and anterior 107 sections can be rigidly connected to one another and can be disconnected by respectively severing each of connecting members 121b, 123a, 123b. Connecting members 121, 123 are configured such that an intermediate portion thereof is spaced away from surgical guide 100 and/or the patient's bone 3, thereby allowing the connecting members 121, 123 to be readily severed using a severing tool (such as a saw or scissors, for example) while minimizing a risk of damaging surgical guide 100 or bone 3. In the present configuration, connecting members 121b, 123a, 123b loop away from the surgical guide 100 and comprise a rounded intermediate section spaced away from surgical guide 100. Although a particular configuration of connecting members 121, 123 has been shown, it is appreciated that other configurations are possible. In other embodiments, connecting members 121, 123 can have different shapes, and can include different connecting elements. For example, in some embodiments, instead of being fused and/or an integral part of lateral 105 and/or anterior 107 sections, connecting members 121, 123 can be separate pieces removably engageable in lateral 105 and/or anterior 107 sections. As can be further appreciated, in other embodiments, a different number of connecting members 121, 123 can be provided, and they can be positioned differently.

As mentioned above, the surgical guide 100 comprises a plurality of modules to guide various surgical tools used throughout the osteotomy procedure. Each module can perform a different function for assisting with various tasks throughout an osteotomy procedure. Some modules can form integral parts of the lateral 105 and/or anterior 107 sections secured directly to the patient's bone 3, whereas other modules can be independent elements which can be secured to relative to the patient's bone 3 by attaching to lateral 105 and/or anterior 107 sections. Although a particular set of modules will be described in detail hereinafter, it is appreciated that other modules and combinations thereof are possible depending on the requirements of the surgical procedure. Moreover, although some modules are described as performing particular functions, it is appreciated that some modules can perform two or more functions and/or have other advantages or uses not explicitly described herein, but that would be readily understood by a person of skill in the art upon reading the present disclosure.

Anchor Module

Figure 2A:
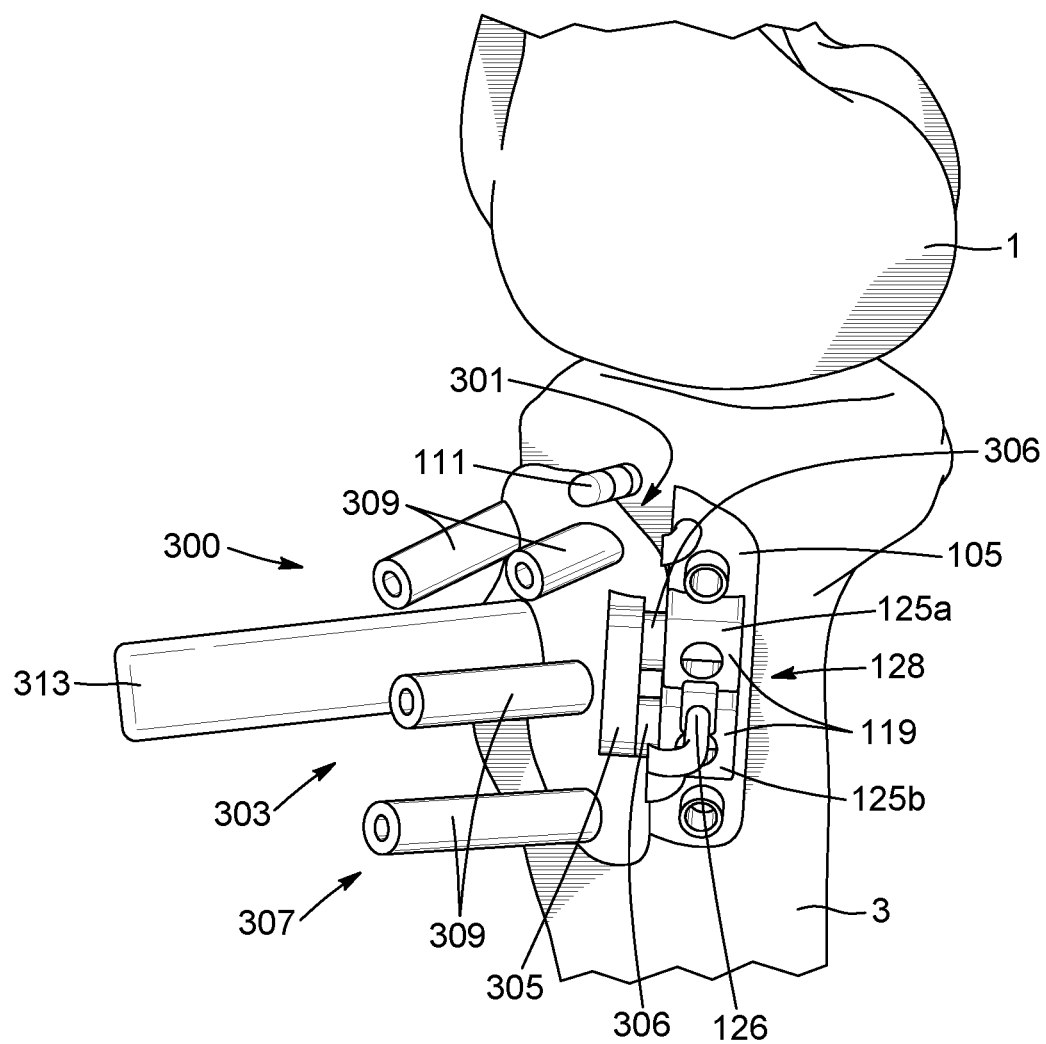
FIGS. 2A and 2B are respectively medial and anterior perspective views of a predrilling module secured to an anchor module on the patient's tibia bone, according to an embodiment.

With reference now to FIG. 2A, an anchor module 119 is provided to anchor removable modules relative to the patient's bone 3. In the present embodiment, anchor module 119 is provided in the lateral section 105 of the surgical guide 100, but it is appreciated that in other embodiments, anchor module 119 can be provided in a different section of guide 100. Moreover, in some embodiments, a plurality of anchor modules can be provided. The anchor module 119 is affixed directly to the patient's bone 3 via fasteners 109 and comprises a removable module interface 128 for interfacing with removable modules. The anchor module can thus act as a secure base to which other modules can be removably attached, allowing the removable modules to be properly aligned relative to the patient's bone 3 at relevant steps during the surgical procedure. In the present embodiment, the removable module interface 128 comprises apertures for receiving corresponding protrusions extending from a removable module, although it is appreciated that other removable connection interfaces are possible.

In the present embodiment, the anchor module 119 comprises two sections for providing two distinct anchoring points. More specifically, the anchor module 119 comprises a proximal section 125*a* positioned proximate the joint between the patient's femur 1 and tibia 3 bones, and a distal section 125*b* spaced further away from the joint between the femur 1 and tibia 3. The proximal 125*a* and distal 125*b* sections are separable from one another, allowing them to move independently while being secured to different sections of the patient's bone 3. In the present embodiment, proximal 125*a* and distal 125*b* sections are secured to one another via connecting member 126. The connecting member 126 can be severed to separate proximal 125*a* and distal 125*b* sections and allow them to move independently with different sections of bone. For example, in the present embodiment, proximal 125*a* and distal 125*b* sections are positioned on the patient's bone 3 on opposite sides of a planar cut formed therein as part of the surgical procedure. After the planar cut is formed, connecting member 126 can be severed to separate proximal 125*a* and distal 125*b* sections. The bone 3 can be opened along the planar cut, with the proximal 125*a* and distal 125*b* sections moving away from one another while being respectively connected to the bone 3 above and below the opening formed in the bone 3. In this fashion, the proximal section 125*a* can provide an anchoring point above or proximal the opening in the bone 3, while the distal section 125*b* provides an anchoring point below or distal the opening in the bone 3. It is appreciated that other positions and configurations of anchor module 119 and corresponding sections are possible, depending on the surgical procedure. It is further appreciated that the separable sections of anchor module 119 can be connected to one another via different removable connection mechanisms.

Predrilling Module

Figure 2B:
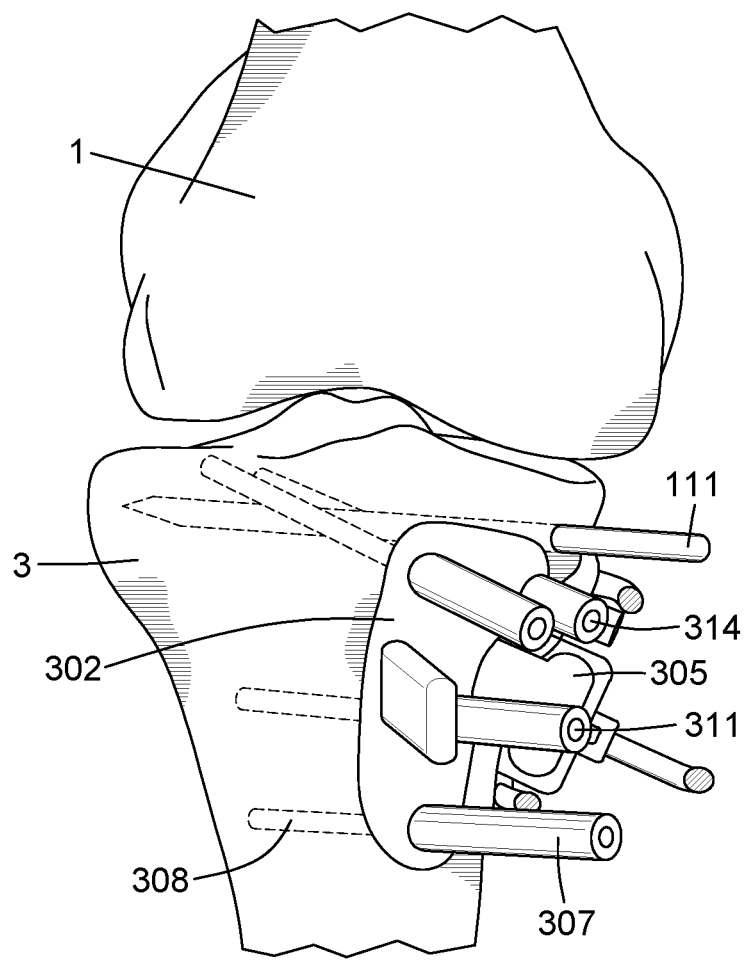

With reference to FIGS. 2A and 2B, a predrilling module 300 is provided for predrilling holes in the patient's bone 3 for eventually receiving fasteners to secure a plate or other implant to the patient's bone 3. The predrilling module 300 is patient-specific in that it is custom made according to the anatomy of the patient's bone 3 and according to a preoperative plan. In this fashion, the predrilling module 300 can be configured to precisely fit on a predetermined position of the patient's bone 3 to assure proper alignment, and to assist in drilling holes in the patient's bone 3 in predetermined positions, orientations and depths.

In the illustrated embodiment, the predrilling module 300 comprises a body 302 having a bone interface side 301 and an operative side 303. The bone interface side 301 comprises a bone-contacting surface having contours complementary in shape to the surface contours of the patient's bone 3. In this configuration, bone interface side 301 can abut against the patient's bone 3, and key into a specific position thereon.

In the present embodiment, bone interface side 301 comprises a solid surface, however it is appreciated that other configurations are possible. For example, the surface can be defined by an open lattice, and can comprise edges conforming to the contours of the patient's bone 3.

The operative side 303 is provided opposite the bone interface side 301 and comprises a plurality of drill guides 307 extending therefrom for guiding corresponding drill bits. In the present embodiment, the drill guides 307 each comprise a guide barrel 309 extending from the body of the predrilling module 303 at a predetermined angle along a lengthwise axis and terminating at a terminal end 314. The guide barrel 309 comprises sidewalls defining a hollow interior in the form of a guide tunnel 311 extending through the guide barrel 309 along the lengthwise axis thereof and opening on the bone interface side 301 and operative side 303 of predrilling module 303. The guide tunnels 311 are sized and shaped to receive a corresponding drill bit therein, allowing the drill bit to slide in and out of barrel 309, while sidewalls of barrel 309 constrain movement of the drill bit to a predetermined depth, position, and orientation relative to the patient's bone 3. An abutting member on the drill bit can limit an insertion depth of an operative end of the drill bit into the barrel 309 as it abuts with terminal end 314 of guide barrel 309. As can be appreciated, in this configuration, the length of barrel 309 can limit insertion depth of a drill bit and assure the depth of drill holes formed therewith.

The plurality of drill guides 307 are configured to cooperate with a calibrated drill bit having a fixed operative length. The guide barrels 309 of the drill guides 307 are sized, positioned and oriented to create drill holes 308 in a predefined pattern for receiving fasteners to secure an implant, such as plate, to the patient's bone 3. As will be described in more detail hereinafter, the implant to be secured can be patient-specific and can be designed to be affixed using different types of fasteners. Based on the anatomy of the patient's bone 3, a preoperative plan can define a configuration of fasteners, including size, depth, orientation, and position, such that the implant can be affixed optimally. The drill guides 307 can thus be configured to guide drill bits to form drill holes 308 in preparation for receiving the configuration of fasteners defined in the preoperative plan. For example, the length of each guide barrel 309 can be adjusted to limit the insertion depth of the drill bit, creating drill holes 308 with different predetermined depths. Similarly, the position an orientation of guide barrels 309 can be adjusted to define drill holes 308 which extend at different angles and positions. Finally, diameters of guide tunnels 311 can be adjusted to accommodate drill bits of different diameters to create drill holes of different sized for accommodating different sizes of fasteners.

In the present embodiment, the predrilling module 300 is configured to predrill holes 308 in the patient's bone 3 prior to a surgical alteration of the bone's geometry. The predrilling module 300 is thus configured to account for the drill holes 308 moving as the geometry of the bone is altered during surgery, such that the drill holes 308 will be in alignment with the fasteners of an implant once the bone alterations are complete. For example, in the context of a high-tibial open-wedge osteotomy procedure, the predrilling module 300 can be configured to predrill holes while the patient's bone 3 is in a closed configuration (i.e. before the patient's bone 3 is opened along the planar cut formed using the drilling 113 and cutting 117 modules). In this configuration, the guide barrels 309 are positioned to form drill holes 308 which will eventually align with the location of fasteners for affixing an implant once the patient's bone 3 is opened along the planar cut to an opened configuration. As can be appreciated, the required position of drill holes 308 can be determined by modelling the patient's bone 3, virtually opening the bone model to a desired opening angle, and virtually positioning an implant and corresponding fasteners on the bone model to set final positions of the drill holes 308. The bone model can be subsequently closed virtually to determine corresponding initial positions of the drill holes 308. The predrilling module 300 can then be designed according to the initial positions of the drill holes 308.

As shown in FIGS. 2A and 2B, predrilling module 300 comprises an attachment/alignment mechanism 305 for securing the predrilling module 300 relative to the patient's bone 3 and/or for assuring proper alignment of the predrilling module 300 relative to the patient's bone 3. In the present embodiment, the attachment/alignment mechanism 305 comprises an attachment interface for interfacing with removable module interface 128 in anchor module 119. The attachment/alignment mechanisms 305 is configured such that the predrilling module 300 can attach to anchor module 119 in only one position/orientation, thus assuring that predrilling module 300 is properly aligned once it is attached to anchor module 119. For example, in the present embodiment, the attachment interface comprises two protrusions or pins 306 sized and shaped to engage in corresponding apertures in anchor module 119. The protrusions 306 provide two fixed attachment points which must be respectively align with two fixed anchoring points in the anchor module 119 for the predrilling module 300 to engage with anchor module 119. In the present embodiment, the protrusions 306 are positioned to align with anchor module 119 while the patient's bone 3 is in a closed configuration, thereby allowing the predrilling module 300 to engage with the patient's bone 3 and predrill holes 308 prior to opening the bone 3 (i.e. the protrusions 306 respectively align with the proximal 125a and distal 125b sections while they are adjacent one another). It is appreciated that in other embodiments, the protrusions 306 can be positioned to align with the anchor module 119 when the patient's bone is in the opened configurations (i.e. when the proximal 125a and distal 125b sections are space apart from one another across the opening in the patient's bone 3).

Although in the present embodiment a single mechanism 305 provides both the functions of securing and aligning predrilling module 300 relative to the patient's bone 3, it is appreciated that in other embodiments, different mechanisms can be provided to align and/or to secure predrilling module 300, and that separate mechanisms can be provided to respectively perform the alignment or attachment functions. For example, in some embodiments, predrilling module 300 can be secured to the patient's bone directly via fasteners. In some embodiments, the bone interface side 301 of predrilling module 300 can be shaped to have contours complementary in shape to the contours of a specific area of the patient's bone 3. In some embodiments, mechanism 305 can comprise a member configured to interlace and/or insert into a hole or other feature formed in the patient's bone 3, for example in the opening formed along the planar cut.

The predrilling module 300 further comprises a handle member 313 which allows the module 300 to be more easily manipulated and positioned. In the present embodiment, the handle member 313 is a rigid elongated member extending from the body of the predrilling module 300 along a lengthwise axis and facilitates manipulation of the module 300 by hand. It is appreciated that in other embodiments, different types of handle members can be provided. For example, handle member can be removable and/or can comprise an interlace for a positioning tool or guide. In the present embodiment, the handle member 313 has inscriptions provided thereon to identify the predrilling module 300 and/or to indicate the type of drill bits with which the predrilling module 300 is designed to cooperate.

Figure 3:
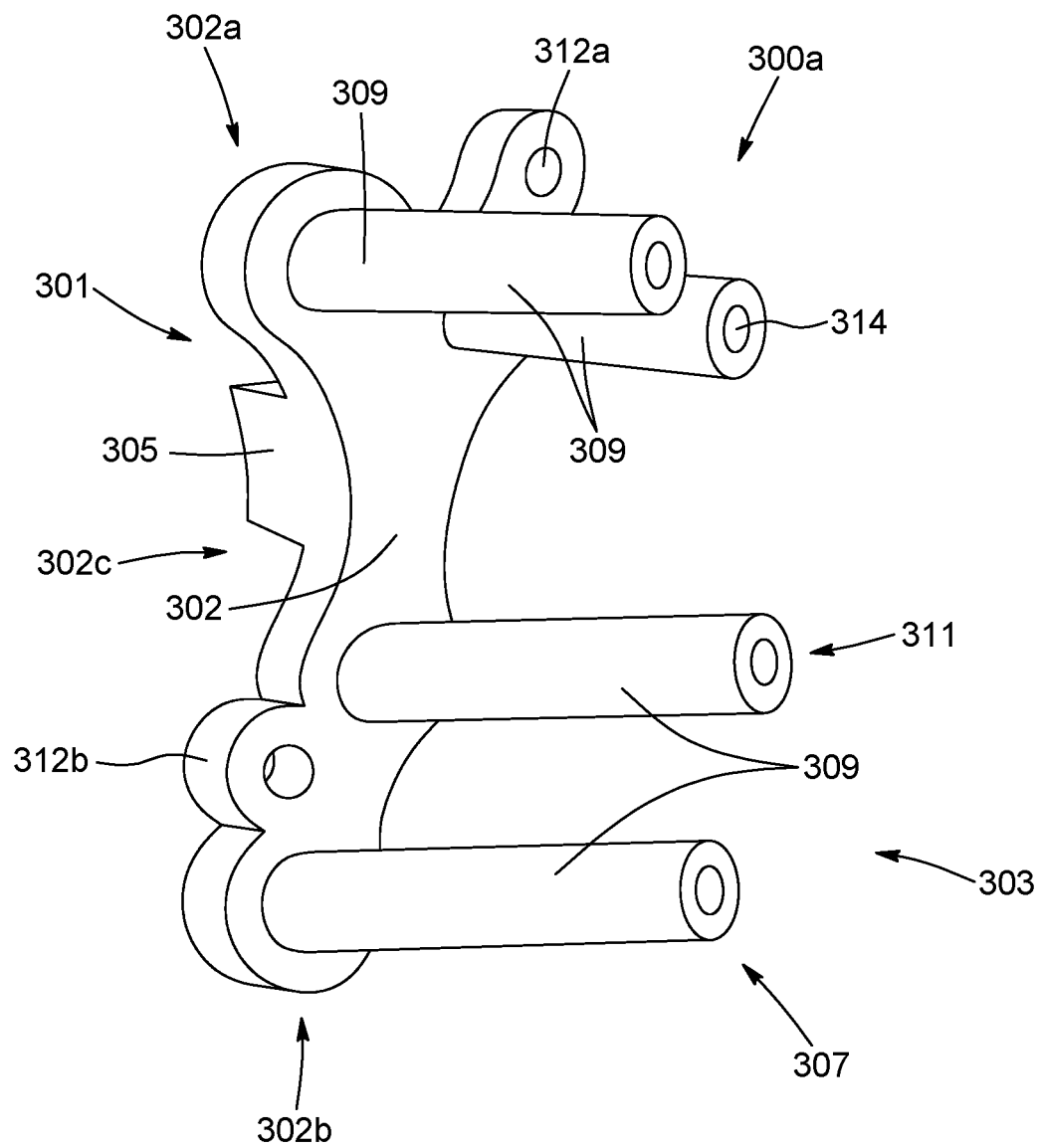
FIG. 3 is a perspective view of a predrilling module, according to an alternate embodiment in which the predrilling module is configured to drill holes for the fixation plate after an open wedge has been formed in the patient's bone.

Although in the illustrated embodiment the predrilling module 300 is configured to drill holes 308 prior to a change in the geometry of the patient's bone 3, it is appreciated that the predrilling module 300 can be configured differently according to the requirements of the surgical procedure. For example, as shown in FIG. 3, an embodiment of a predrilling module 300a is shown in which the module 300a is configured to drill holes 308 after the geometry of the patient's bone 3 has been surgically altered. In this embodiment, the predrilling module 300a is configured to span across opening 7 formed in the patient's bone 3, and position drill guides 307 to define drill holes 308 directly in their final position. More specifically, the predrilling module 300a has a body 302 substantially similar to a fixation plate which will ultimately be used to secure the opening 7 in the patient's bone 3. The bone 3 can thus be opened along planar cut 5 to form opening 7, and once the opening 7 is formed, the predrilling module 300 can be secured to the bone at the same position where the fixation plate will eventually be attached. The predrilling module 300 will thus have its drill guides 307 positioned exactly where the fastener apertures of fixation plate will eventually be positioned. Therefore, after drill holes 308 are formed, predrilling module 300 can be removed and replaced with fixation plate. Fixation plate can be positioned to align with the holes 308 and then secured in place via fasteners.

In the present embodiment, the body 302 of predrilling module 300 has a bone interface side 301 having a bone-contacting surface substantially conforming to a surface contour of the patient's bone 3 at a predetermined position. The body 302 is configured with a proximal section 302a for positioning adjacent a surface of the patient's bone 3 above opening 7, a distal section 302b for positioning adjacent a surface of the patient's bone 3 below opening 7, and an intermediate section 302c for spanning the opening 7. The attachment/alignment mechanism 305 comprises a wedge extending from bone interface side 301 on the intermediate section 302c of body 302, and configured to be inserted into the opening 7. As can be appreciated, wedge 305 can be sized and shaped according to the expected dimensions of the desired opening 7 according to a preoperative plan. It can further comprise contours matching inner surface contours of the opening 7, as will be described in more detail below in connection with the opening validator. The wedge 305 can thus allow predrilling module 300 to secure at a predetermined position relative to opening 7, while also validating that the bone 3 has been opened to the correct angle. Once module 300 has been correctly positioned, it can be secured in place relative to the patient's bone 3 before drilling is performed through drill guides 307. In the present embodiment, the body 302 comprises fastener apertures 312a, 312b in the proximal 302a and distal 302b sections to allow the body 302 to be secured directly to the patient's bone 3 via fasteners. It is appreciated, however, that other attachment mechanism are possible. For example, the module 300 could secure to an anchor module already attached to the patient's bone 3 at the correct position.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

The invention claimed is:

1. A guide for guiding drill bits to form holes in a bone, having a planar cut extending therethrough, in a predetermined pattern for receiving fasteners to secure an implant to the bone, the guide comprising:
   a guide body having a first portion, a second portion, an operative side, and a bone interface side opposite the operative side, the bone interface side comprising a bone contacting surface, the bone contacting surface of the first portion of the guide body being engageable with a surface of the bone on a first side of the planar cut and the bone contacting surface of the second portion of the guide body being engageable with a surface of the bone on a second side of the planar cut;
   a plurality of drill guides extending from the operative side of the guide body for guiding corresponding drill bits, the plurality of drill guides comprising at least two first guide barrels protruding from the first portion of the guide body and positioned to assist in forming holes on the first side of the planar cut formed in the bone, and at least two second guide barrels protruding from the second portion of the guide body and positioned to assist in forming holes on the second side of the planar cut; and
   a handle member connected to the guide body and extending from the operative side thereof to facilitate manipulation and positioning of the guide body on the surface of the bone,
   wherein the bone contacting surface of the guide body is configured to substantially conform to surface contours of the bone at a predetermined position on the bone.

2. The guide according to claim 1, wherein the guide barrels extend from the operative side along respective lengthwise axes and terminating at respective terminal ends.

3. The guide according to claim 2, wherein the guide barrels extend from the operative side at predetermined angles and are positioned on the operative side according to the predetermined pattern.

4. The guide according to claim 2, wherein each guide barrel comprises sidewalls defining a guide tunnel extending through the guide barrel along the lengthwise axis, the guide tunnel having openings on the bone interface side and operative side of the guide body configured to receive a corresponding drill bit therethrough.

5. The guide according to claim 4, wherein the sidewalls are adapted to constrain movement of the drill bit to a predetermined depth, position and/or orientation relative to the bone.

6. The guide according to claim 1, wherein the guide body further comprises fastener apertures for receiving fasteners to secure the guide body to the bone.

7. The guide according to claim 1, wherein the guide body is adapted to span across an opening formed along the planar cut, and comprises a proximal section positioned above the opening and a distal section positioned below the opening.

8. The guide according to claim 7, wherein the guide body further comprises an intermediate section spanning the opening between the proximal and distal sections, and an alignment mechanism extending from the intermediate section for engaging the bone to secure the guide body in a predetermined position relative to the bone.

9. The guide according to claim 8, wherein the alignment mechanism comprises a wedge extending from the intermediate section adapted to be inserted within the opening.

10. The guide according to claim 9, wherein the wedge comprises contours configured to match inner surface contours of the opening.

11. The guide according to claim 1, wherein the guide body comprises an alignment mechanism configured to engage with an anchor module secured on a surface of the bone and spanning transversely across the planar cut.

12. The guide according to claim 11, wherein the alignment mechanism comprises an attachment interface for respectively interfacing with anchoring points of the anchoring module positioned on either side of the planar cut.

13. The guide according to claim 12, wherein the attachment interface is configured to interface with the anchoring points in only one orientation.

14. The guide according to claim 12, wherein the anchoring points comprise apertures, and wherein the attachment interface comprises protrusions configured to respectively engage in the apertures.

15. The guide according to claim 1, wherein the guide is configured to assist in forming holes in the bone in initial positions prior to a planned alteration of a geometry of the bone which will cause the drill holes to move into final positions in alignment with fastener apertures in the implant.

16. The guide according to claim 1, wherein the guide is made from 3D-printable material.

17. A method of designing the guide according to claim 1 for guiding drill bits to form holes in a bone in a predetermined pattern for securing a knee osteotomy implant on the bone prior to altering a geometry of the bone, the method comprising the steps of:
   creating a digital 3D model of the bone;
   virtually cutting the 3D model of the bone to form a planar cut therein;
   virtually opening the 3D model of the bone along the planar cut to a desired opening angle;
   virtually positioning a knee osteotomy implant and corresponding fasteners on the 3D model of the bone to set final positions of drill holes;
   virtually closing the 3D model of the bone to determine corresponding initial positions of the drill holes; and
   designing the guide with drill guides positioned according to the initial positions of the drill holes.

18. A guide for assisting in forming holes in a bone, having a planar cut extending therethrough, according to a predetermined pattern for receiving fasteners to secure an implant on the bone, the guide comprising:
   a guide body having a first portion, a second portion, an operative side and a bone interface side opposite the operative side, the bone interface side comprising a bone contacting surface, the bone contacting surface of the first portion of the guide body being engageable with a surface of the bone on a first side of the planar cut and the bone contacting surface of the second portion of the guide body being engageable with a surface of the bone on a second side of the planar cut;
   a plurality of drill guides connected to the operative side of the guide body for guiding corresponding drill bits adapted to form the holes, the plurality of drill guides comprising at least two first guide barrels protruding from the first portion of the guide body and positioned to assist in forming holes on the first side of the planar cut formed in the bone, and at least two second guide barrels protruding from the second portion of the guide body and positioned to assist in forming holes on the second side of the planar cut; and a handle member connected to the guide body and extending from the operative side thereof to facilitate manipulation and positioning of the guide body on the surface of the bone, wherein the drill guides are positioned to guide the drill bits to form the holes in the bone in initial positions prior to a planned alteration of a geometry of the bone which will cause the holes to move into final positions in alignment with fastener apertures in the implant.

\* \* \* \* \*